United States Patent [19]

Wright

[11] 4,252,813
[45] Feb. 24, 1981

[54] OXAMIDES, PHARMACEUTICAL COMPOSITIONS THEREOF AND METHOD OF USE

[75] Inventor: John B. Wright, Kalamazoo, Mich.

[73] Assignee: The Upjohn Company, Kalamazoo, Mich.

[21] Appl. No.: 95,217

[22] Filed: Nov. 19, 1979

[51] Int. Cl.³ ............... A61K 31/44; C07D 213/75
[52] U.S. Cl. .................... 424/263; 424/304;
424/321; 260/465 D; 546/287; 546/288;
546/289; 546/292; 546/308; 564/96; 564/98;
564/82
[58] Field of Search ........... 260/556 AC, 465 D;
546/292, 308, 289, 288, 287; 424/263, 304, 321

[56] References Cited

U.S. PATENT DOCUMENTS

| 3,962,308 | 6/1976 | Sinkula | 546/308 |
| 3,980,660 | 9/1976 | Wright et al. | 546/308 |
| 4,038,398 | 7/1977 | Hall et al. | 546/308 |

Primary Examiner—Henry R. Jiles
Assistant Examiner—Robert T. Bond
Attorney, Agent, or Firm—Martin B. Barancik

[57] ABSTRACT

Compounds of the formula

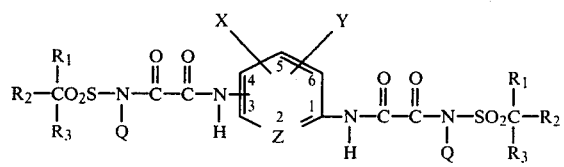

are useful as anti-allergy agents.

20 Claims, No Drawings

OXAMIDES, PHARMACEUTICAL COMPOSITIONS THEREOF AND METHOD OF USE

BRIEF SUMMARY OF THE INVENTION

It has now been discovered that novel compounds of FIG. 1 are useful in the prophylactic treatment of sensitized humans and animals for allergy and all anaphylactic reactions of a reagin or non-reagin mediated nature. The compounds are formulated with pharmaceutical carriers for oral, parenteral or inhalation means of administration.

DETAILED DESCRIPTION OF THE INVENTION

In accordance with this invention is provided compounds represented by Formula I and hereafter referred to as Group A Formula I

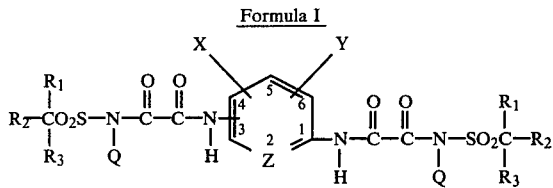

wherein X and Y are the same or different and are hydrogen, alkyl of one to six carbon atoms, inclusive, alkoxy of one to six carbon atoms, inclusive, halo, cyano, nitro, trifluoromethyl and

$R_1$, $R_2$ and $R_3$ are the same or different and are hydrogen, fluoro or chloro;

Q is hydrogen or a pharmacologically acceptable metal or amine cation; the second

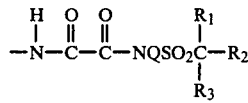

is at the 3 or 4 position;

and Z is N, C—H, C—X or C—Y with the proviso that when Z is N, then X and Y are hydrogen, and the second

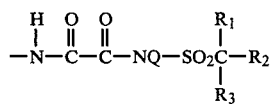

is at the 3-position;

A further group of compounds hereafter referred to as Group B in the invention are compounds of Group A wherein X and Y are the same or different and are hydrogen, alkyl of one to three carbon atoms, inclusive, alkoxy of one to three carbon atoms, inclusive, fluoro, chloro, cyano, nitro, trifluoromethyl and

Another group of compounds hereafter referred to as Group C are the compounds of Group A wherein $R_1$, $R_2$ and $R_3$ are the same.

A further group of compounds hereafter referred to as Group D are the compounds of Group B wherein $R_1$, $R_2$ and $R_3$ are the same.

Another group of compounds hereafter referred to as Group E are the compounds of Group D wherein Z is C—X; Y is at the 5-position and the second

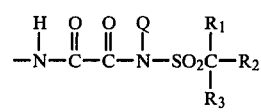

is at the 3-position.

A further group of compounds hereafter referred to as Group F are compounds of Group E wherein X is hydrogen.

Another group of compounds hereafter referred to as Group G are compounds of Group E wherein Y is hydrogen.

A further group of compounds are compounds of Groups E, F and G, wherein $R_1$, $R_2$ and $R_3$ are hydrogen.

Another group of compounds are those compounds of Groups E and F wherein Q is hydrogen.

A further group of compounds are those compounds of Groups E and F wherein Q is a pharmacologically acceptable metal or amine cation.

The preferred compound is N,N″-(2-chloro-5-cyano-m-phenylene)bis[N′-(methylsulfony)oxamide] and its salts.

As employed in the above disclosure and throughout the specification and claims, the phrase "alkyl of one to six carbon atoms" includes methyl, ethyl, propyl, butyl, pentyl, hexyl and isomers thereof. Illustrative examples of isomers are isopropyl, tert butyl, neopentyl and 2,2-dimethylbutyl. Alkyl of a smaller number of carbon atoms has a similar scoping. "Halo" include fluoro, chloro, bromo and iodo. The pharmacologically acceptable amine refers to amines which are accepted by mammals in an essentially non-toxic manner when administered to mammals in conjunction with the acid moiety of the invention.

Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucoseamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "pharmacologically acceptable metal" includes alkali metals such as sodium and potassium, alkaline earth metals such as calcium and magnesium, and other acceptable metals such as aluminum.

The compounds of this invention are prepared through the following reaction sequence, see Chart 1. The various known or readily prepared sulfonylamines (III) is each reacted with an excess of oxalyl chloride (IV) to form the oxalyl acid chloride of the sulfonylamine (V). This compound is then reacted with the known X and Y substituted m- or p-phenylene diamine (VI) to form the claimed N,N''-(phenylene)bis[N'-(methyl or halosulfonyl)oxamide] (VII).

The addition of excess oxalyl chloride to sulfonylamine is well known in the art, Frang and Osuch, J. Org. Chem. 29, 2592 (1964). The excess oxalyl chloride can serve as solvent however cosolvents such as benzene, toluene, chloroform and ethylene chloride can also be used. Room temperature or slightly elevated temperature can be employed with facility in the reaction.

The conversion of the oxalyl acid chloride sulfonylamine (V) to the compounds of the invention appears to be a new reaction. The reaction is carried out in a solvent such as ethylacetate, pyridine, dimethylformamide, dimethyl acetamide and the like. The temperature can be anywhere from 0° to about 100° C., the temperature depending at least partially upon the desired reaction time which can vary from 1 to about 24 hours.

The halosulfonylamides are readily prepared by reacting a halogenated methyl sulfonyl acid halide with ammonia. Various known reagents are dichloromethanesulfonamide and difluoromethanesulfonamide. Mixed halomethane sulfonamides are readily prepared by standard techniques.

The sulfonamides are converted to the salts by reaction of the said compound with an equivalent of the particular base desired.

In Chart 2 are illustrative examples of compounds in accordance with the invention.

It should be noted that the exemplification of Chart 2 is with Q as hydrogen. Any salts of the compounds are readily prepared by standard techniques.

Below are specific examples of the invention. These examples are not intended to limit the invention.

EXAMPLE 1

N,N'-m-phenylenebis[N'-(methylsulfonyl)oxamide]

A mixture of 9.50 gm (0.1 mole) of methanesulfonamide and 63.5 gm (0.5 mole) of oxalyl chloride is refluxed for 45 minutes and allowed to stand at room temperature overnight. To the mixture there is added an equal volume of hexane and the mixture triturated. The insoluble material is removed by filtration. There is obtained 16.3 gm (86%) of a white solid melting at 95° C. (dec.).

To a stirred solution of 3.89 gm (0.036 mole) of m-phenylenediamine in 200 ml of ethyl acetate is added 16.3 gm (0.083 mole) of the acid chloride obtained above. The mixture is cooled in an ice-bath and there is added 8.90 gm of triethylamine. The reaction mixture is allowed to stand overnight at room temperature.

The precipitate is removed by filtration and stirred with 400 ml of water. The insoluble material is removed by filtration. The precipitate is dissolved in a solution of 10.17 gm (0.084 mole) of tris(hydroxymethyl)aminomethane (THAM) in 200 ml of water. The solution is acidified with glacial acetic acid. The precipitate is removed by filtration.

The precipitate is dissolved in a solution of 1.2 gm of sodium hydroxide in 100 ml of water. The solution is filtered and acidified with glacial acetic acid. The precipitate is removed by filtration and washed with water. There is obtained 8.11 gm of cream colored solid melting at > 300°.

Analysis: Calc'd. for $C_{12}H_{14}N_4O_8S_2$: C, 35.46; H, 3.47; N, 13.78; S, 15.78%.

Found: C, 35.43; H, 3.68; N, 13.65; S, 15.85%.

EXAMPLE 2

N,N''-2,6-Pyridinediylbis[N'-(methylsulfonyl)oxamide]

A mixture of 9.50 gm (0.1 mole) of methanesulfonamide and 63.5 gm of oxalyl chloride is refluxed 45 minutes and cooled to room temperature. To the mixture there is added an equal volume of hexane. The insoluble material is removed by filtration. There is obtained 14.6 gm of white solid melting at 94°–96° C. (dec.). To a stirred solution of 2.18 gm (0.02 mole) of 2,6-diaminopyridine in 150 ml of dry ethyl acetate is added 9.80 gm (0.053 mole) of the above acid chloride. The mixture is cooled in an ice-bath and there is added slowly, 5.36 gm (0.053 mole) of triethylamine. The reaction mixture is allowed to warm to room temperature and to stand overnight.

The precipitate is removed by filtration and stirred with 400 ml of water. The insoluble material is removed by filtration. There is obtained 1.65 gm of green solid melting at > 300° C.

Analysis: Calc'd. for $C_{11}H_{13}N_5S_2O_8$: C, 32.43; H, 3.21; N, 17.19; S, 15.74%.

Found: C, 33.22; H, 3.57; N, 17.47; S, 15.22%.

EXAMPLE 3

N,N''-(2-Chloro-5-cyano-m-phenylene)bis[N'-(methylsulfonyl)oxamide]

A mixture of 9.50 gm (0.1 mole) of methanesulfonamide and 63.5 gm (0.5 mole) of oxalyl chloride is refluxed for 45 minutes. The mixture is allowed to stand at room temperature overnight. To the mixture there is added an equal volume of hexane and the mixture is triturated. The insoluble material is removed by filtration. There is obtained 14.6 gm of white solid melting at 94°–96° C. (dec.).

To a stirred solution of 1.67 gm (0.01 mole) of 4-chloro-3,5-diaminobenzonitrile in 80 ml of ethyl acetate is added 4.64 gm (0.025 mole) of the above acid chloride. The mixture is cooled in an ice-bath and there is added 2.53 gm (0.025 mole) of triethylamine. The reaction mixture is allowed to warm to room temperature and to stand overnight.

The precipitate is removed by filtration and stirred with 400 ml of water. The insoluble material is removed by filtration. There is obtained 3.55 gm of white solid melting at > 300° C.

Analysis: Calc'd. for $C_{13}H_{12}Cl\ N_5S_2O_8$: C, 33.51; H, 2.59; N, 15.03; Cl, 7.61; S, 13.76%.

Found: C, 33.52; H, 2.68; N, 14.60; Cl, 7.58; S, 13.40%.

The compositions of the present invention are presented for administration to humans and animals in unit dosage forms, such as tablets, capsules, pills, powders, granules, sterile parenteral solutions or suspensions, eye drops, oral solutions or suspensions, and oil in water and water in oil emulsions containing suitable quantities of the compound of Formula I.

For oral administration, either solid or fluid unit dosage forms can be prepared. For preparing solid compositions such as tablets, the compound of FIG. 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For treatment of allergic conditions of the nose, such as rhinitis, compositions adapted for contact with nasal linings are preferred.

Compositions for inhalation are of three basic types:

(1) a powder mixture preferably micropulverized with particle size, preferably from about 1 to about 5 microns;

(2) an aqueous solution to be sprayed with a nebulizer; and (3) an aerosol with volatile propellant in a pressurized container.

The powders are quite simply prepared by mixing a compound of Formula I with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be nontoxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluormethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, coated tablets, powder packets, wafers, granulates, cachets, teaspoonfuls, tablespoonfuls, dropperfuls, ampoules, vials, aerosols with metered discharges, segregated multiples of any of the foregoing, and other forms as herein described.

Oral delivery systems with compounds of the invention are employed. Those delivery systems with solid pharmaceutical carriers can be used as an appropriate vehicle. Liquid pharmaceutical carriers can also be used as an appropriate vehicle. These liquid vehicles are separated into aqueous and non-aqueous systems. Oral unit dosage forms which are preferred are tablets, capsules, pills and powders. Liquid carriers can be divided into a unit dosage by the potential recipient of the drug, for example, droppersful, teaspoonsful, tablespoonsful, and unit dosages of other magnitude.

An effective but non-toxic quantity of the compound is employed in treatment. The dosage of the compound for treatment depends on the route of administration and the potency of the particular compound. A dosage schedule for humans of from about 0.05 to about 50 mg. of compound in a single does, administered parenterally or by inhalation in the compositions of this invention are effective for preventing allergy attacks. More specifically, the single dose is from about 0.5 to about 5 mg. of compound. The oral dose is from about 0.1 to about 100 mg. in a single dose. More specifically, the single dose is from about 1 to about 40 mg. of compound. The dosage to be administered can be repeated up to four times daily.

The administration of the composition of the present invention to humans and animals provides a method for the prophylactic treatment of allergy and an phylactoid reactions of a reagin or non-reagin, preferably reagin, mediated nature. That is to say, these compositions, when administered to a sensitized individual prior to the time that the individual comes into contact with substances (antigens) to which he is allergic, will prevent the allergic reaction which would otherwise occur. It is believed that the compounds of Formula I function as inhibitors of the release of pharmacological mediators of anaphylaxis following antigen-antibody combination.

For example, the process can be used for treatment of such conditions as bronchial asthma, allergic rhinitis, food allergy, urticaria, exercise or stress induced asthma, anaphylactoid reactions and bird fancier's disease. Preferred conditions for treatment are bronchial asthma, allergic rhinitis, food allergy and urticaria. More preferred conditions are bronchial asthma and allergic rhinitis.

EXAMPLE 4

A lot of 10,000 tablets each containing 20 mg of N,N''-(2-chloro-5-cyano-m-phenylene)bis[N'-(methylsulfonyl)oxamide] is prepared from the following types and amounts of ingredients:

| | |
|---|---|
| N,N''-(2-chloro-5-cyano-m-phenylene)-bis[N'-(methylsulfonyl)oxamide] | 200 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium Stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets. These tablets are useful in preventing or reducing the severity of bronchial asthma attacks when taken at a dose of one tablet every four to six hours.

EXAMPLE 5

A sterile preparation suitable for intramuscular injection and containing N,N''-(2-chloro-5-cyano-m-phenylene)bis[N'-(methylsulfonyl)oxamide] is prepared from the following ingredients:

| | |
|---|---|
| N,N''-(2-chloro-5-cyano-m-phenylene)-bis[N'-(methylsulfonyl)oxamide] | 20 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for prophylactic treatment of allergic rhinitis.

EXAMPLE 6

An aqueous solution containing 3000 mg. of the ditris (hydroxymethyl)aminomethane salt of N,N''-(2-chloro-5-cyano-m-phenylene)bis[N'-(methylsulfonyl)oxamide] is prepared as follows:

| | |
|---|---|
| Di-tris(hydroxymethyl)aminomethane salt of N,N''-(2-chloro-5-cyano-m-phenylene)bis[N'-(methylsulfonyl)oxamide] | 3 Gm. |
| Sodium chloride | 5 Gm. |
| Water for injection q.s. | 600 ml. |

The THAM salt and sodium chloride are dissolved in sufficient water to make 600 ml. and sterile filtered.

The solution is placed in nebulizers designed to deliver 0.25 ml. of solution per spray.

One spray of the solution is inhaled into the lungs every four to six hours for prevention of asthmatic attack.

EXAMPLE 7

A powder mixture consisting of 0.5 grams of the disodio salt of N,N''-(2-chloro-5-cyano-m-phenylene)-bis-[N'-(methyl-sulfonyl)oxamide] and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 8

After allowing for the different solubilities of the compounds and the activity of the particular compound as measured, for example by the in vivo rat passive cutaneous anaphylaxis assay, a suitable quantity of each of the compounds, assuming appropriate solubility, of Example 1, 2 and Chart 2 is substituted for the active compound in the compositions and uses of Examples 4–7. Results showing anti-allergic activity are obtained.

CHART 1

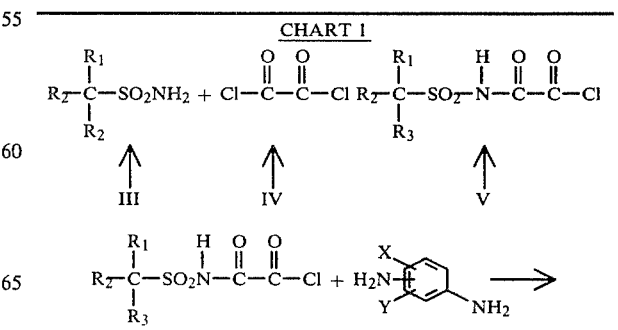

-continued

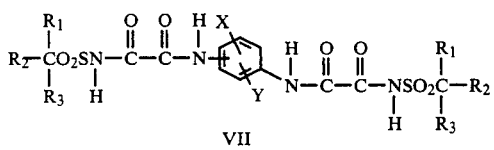

VII

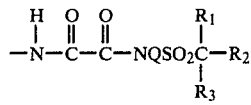

is at the 3 position.

2. A compound in accordance with claim 1 wherein X and Y are the same or different and are hydrogen, alkyl of one to three carbon atoms, inclusive, alkoxy of one to three carbon atoms, inclusive, fluoro, chloro, cyano, nitro, trifluoromethyl and

3. A compound in accordance with claim 1 wherein $R_1$, $R_2$ and $R_3$ are the same.

4. A compound in accordance with claim 2 wherein $R_1$, $R_2$ and $R_3$ are the same.

5. A compound in accordance with claim 4 wherein Z is C—X, Y is at the 5-position and the second

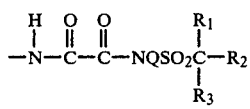

is at the 3-position.

CHART 2

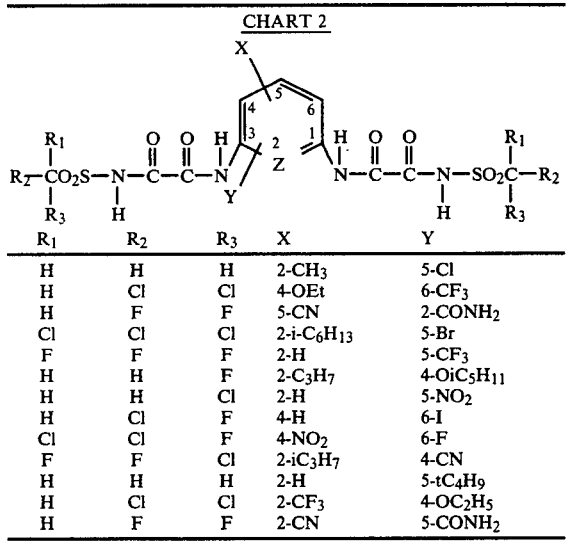

| $R_1$ | $R_2$ | $R_3$ | X | Y |
|---|---|---|---|---|
| H | H | H | 2-CH$_3$ | 5-Cl |
| H | Cl | Cl | 4-OEt | 6-CF$_3$ |
| H | F | F | 5-CN | 2-CONH$_2$ |
| Cl | Cl | Cl | 2-i-C$_6$H$_{13}$ | 5-Br |
| F | F | F | 2-H | 5-CF$_3$ |
| H | H | F | 2-C$_3$H$_7$ | 4-OiC$_5$H$_{11}$ |
| H | H | Cl | 2-H | 5-NO$_2$ |
| H | Cl | F | 4-H | 6-I |
| Cl | Cl | F | 4-NO$_2$ | 6-F |
| F | F | Cl | 2-iC$_3$H$_7$ | 4-CN |
| H | H | H | 2-H | 5-tC$_4$H$_9$ |
| H | Cl | Cl | 2-CF$_3$ | 4-OC$_2$H$_5$ |
| H | F | F | 2-CN | 5-CONH$_2$ |

I claim:

1. A compound of the formula

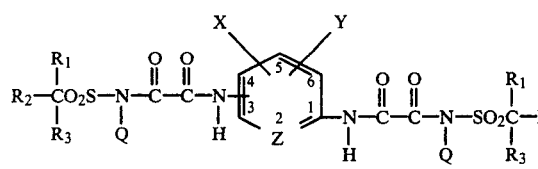

wherein X and Y are the same or different and are hydrogen, alkyl of one to six carbon atoms, inclusive, alkoxy of one to six carbon atoms, inclusive, halo, cyano, nitro, trifluoromethyl and

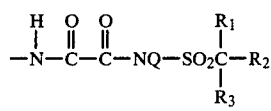

is at the 3 or 4 position;
$R_1$, $R_2$ and $R_3$ are the same or different and are hydrogen, fluoro or chloro;
Q is hydrogen or a pharmacologically acceptable metal or amine cation;
the second —N—C—C—NQ—SO$_2$C—R$_2$ (with H, O, O, R$_1$, R$_3$ substituents)

is at the 3 or 4 position;
and
Z is N, C—H, C—X, C—Y with the proviso that when Z is N, then X and Y are hydrogen and the second 6. A compound in accordance with claim 5 wherein X is hydrogen.

7. A compound in accordance with claim 5 wherein Y is hydrogen.

8. A compound in accordance with claim 5 wherein $R_1$, $R_2$ and $R_3$ are hydrogen.

9. A compound in accordance with claim 6 wherein $R_1$, $R_2$ and $R_3$ are hydrogen.

10. A compound in accordance with claim 7 wherein $R_1$, $R_2$ and $R_3$ are hydrogen.

11. A compound in accordance with claim 5 wherein Q is hydrogen.

12. A compound in accordance with claim 6 wherein Q is hydrogen.

13. A compound in accordance with claim 5 wherein Q is a pharmacologically acceptable metal or amine cation.

14. A compound in accordance with claim 6 wherein Q is a pharmacologically metal or amine cation.

15. N,N''-(2-Chloro-5-cyano-m-phenylene)bis[N'-(methylsulfonyl)oxamide] according to claim 1.

16. Di-tris(hydroxymethyl)aminomethane salt of N,N'''-(2-chloro-5-cyano-m-phenylene)bis[N'-(methylsulfonyl)oxamide] according to claim 1.

17. N,N'-m-Phenylenebis[N'-(methylsulfonyl)oxamide] according to claim 1.

18. N,N'-2,6-pyridinediylbis[N'-(methylsulfonyl)oxamide] according to claim 1.

19. A pharmaceutical composition which comprises an anti-allergy effective amount of a compound of the formula of claim 1 in association with a pharmaceutical carrier.

20. A method for the prophylactic treatment of allergy of a reagin or non-reagin mediated nature which comprises prophylactically administering to a mammal in need of said treatment an anti reagin or non-reagin mediated allergy effective amount of a compound of the formula of claim 1.

* * * * *